(12) United States Patent
Jackson et al.

(10) Patent No.: US 8,356,895 B2
(45) Date of Patent: Jan. 22, 2013

(54) ALL WEATHER SPORT GOGGLE

(75) Inventors: Eleanor Wink Jackson, Boulder, CO (US); Michael T. Jackson, Boulder, CO (US)

(73) Assignee: Zeal Optics, Inc., Boulder, CO (US)

( * ) Notice: Subject to any disclaimer, the term of this patent is extended or adjusted under 35 U.S.C. 154(b) by 247 days.

(21) Appl. No.: 12/812,457

(22) PCT Filed: Jan. 16, 2009

(86) PCT No.: PCT/US2009/031336
§ 371 (c)(1),
(2), (4) Date: Jul. 10, 2010

(87) PCT Pub. No.: WO2009/092043
PCT Pub. Date: Jul. 23, 2009

(65) Prior Publication Data
US 2010/0283956 A1 Nov. 11, 2010

Related U.S. Application Data

(60) Provisional application No. 61/021,826, filed on Jan. 17, 2008.

(51) Int. Cl.
*G02C 7/02* (2006.01)
(52) U.S. Cl. .................................. 351/159.01
(58) Field of Classification Search .............. 351/49, 351/41, 159, 177, 159.01; 2/426, 427, 430, 2/431, 432; 264/2.2, 1.32, 1.7, 1.8
See application file for complete search history.

(56) References Cited

U.S. PATENT DOCUMENTS

| | | | |
|---|---|---|---|
| 3,252,826 A | 5/1966 | Salzinger | |
| 4,170,567 A | 10/1979 | Chu et al. | |
| 4,890,903 A | 1/1990 | Treisman et al. | |
| 4,977,627 A | 12/1990 | Metcalfe et al. | |
| 5,094,520 A | 3/1992 | Reshef et al. | |
| 5,428,411 A | 6/1995 | Kopfer | |
| 5,528,320 A | 6/1996 | Specht et al. | |
| 5,682,212 A | 10/1997 | Maurer et al. | |
| 5,989,628 A | 11/1999 | Haga et al. | |
| 6,019,469 A | 2/2000 | Fecteau et al. | |
| 6,129,435 A | 10/2000 | Reichow et al. | |
| 6,138,286 A | 10/2000 | Robrahn et al. | |
| 6,254,236 B1 | 7/2001 | Fecteau et al. | |
| 7,134,752 B2 | 11/2006 | Perrott et al. | |
| 7,182,460 B2 | 2/2007 | Pierotti | |
| 7,407,283 B2 | 8/2008 | Babineau et al. | |
| 8,177,358 B2 * | 5/2012 | Matera et al. | 351/49 |
| 2005/0243274 A1 | 11/2005 | Chou | |
| 2007/0001327 A1 | 1/2007 | Chiu | |

OTHER PUBLICATIONS

International Search Report dated Mar. 11, 2009, issued in PCT/US2009/031336.
Written Opinion dated Mar. 11, 2009, issued in PCT/US2009/031336.

* cited by examiner

*Primary Examiner* — Hung Dang
(74) *Attorney, Agent, or Firm* — Brinks Hofer Gilson & Lione

(57) ABSTRACT

Embodiments of the present invention include a lens configured to adapt to varying light conditions. The lens comprises a first layer made of a transparent thermoplastic material and a second layer made of a transparent thermoplastic material. The lens also includes a polarized film and a photochromatic film that adjusts to vary the amount of light that is transmitted through the film in response to the amount of ultraviolet radiation received by the film. The lens is thermoformed to have a selected radius of curvature. Embodiments of the lens disclosed herein are adapted for use with a frame that is configured to receive the lens and position the lens proximate a user's face and eyes.

25 Claims, 11 Drawing Sheets

A - A

ALL WEATHER SPORT GOGGLE

PRIORITY CLAIM

The present application is a utility application under 35 U.S.C. §371 and claims the priority and the benefit of PCT/US09/31336 filed Jan. 16, 2009, which in turn is a continuation-in-part and claims the priority and the benefit of U.S. Provisional Patent Application No. 61/021,826, filed Jan. 17, 2008, the disclosure of each being incorporated herein in its entirety by this reference for all purposes.

FIELD

The present application relates to all weather goggles for use in sports, outdoor activities, military, and safety related applications.

BACKGROUND

Goggles have been used to protect a user's eyes while participating in various activities, including outdoor activities and sports, such as skiing and snowboarding, snowmobiling, snowshoeing, shooting, motorcycle and all-terrain vehicle riding, and similar events, as well as military activities and safety goggles when a user requires eye protection.

When used for outdoor activities, goggles protect the user's eyes from inclement weather conditions, such as cold weather and wind. In addition, the goggles protect against snow, ice, rain, and blowing particulate matter, such as sand. Further, goggles, if so configured, may provide protection from sunlight, ultraviolet radiation, and provide improved contrast and reduced glare from the light reflected off various objects.

While most goggles provide either a greater or lesser degree of protection from physical elements, such as the weather and blowing particulate matter, some previous goggles are designed to work best in a particular light condition. If light conditions change, such as with a change in cloudiness or daylight as the day passes, a particular goggle that is well-suited for one light condition becomes less effective in another light condition as the ambient light changes throughout a day.

Instead of relying on only one goggle with a limited range of ability, the user might choose to bring either several goggles or replacement lenses, each goggle or lens designed to work best in a different type of light condition. While this solves the problem of having a goggle and/or lens available that works best in a given light condition, it requires a user to dedicate space and weight to carrying one or more extra goggles and/or lenses. In addition, such a solution requires a user to stop and change the goggles or lenses he or she uses, which may not be practical in certain locations and weather conditions.

Therefore, a need exists for a goggle that provides a user with enhanced visual acuity and contrast in a variety of light conditions. Such a goggle should be light-weight, flexible, scratch and impact resistant.

SUMMARY

Embodiments of the present invention include a lens configured to adapt to varying light conditions. The lens comprises a first layer made of a transparent thermoplastic material and a second layer made of a transparent thermoplastic material. Optionally, the first layer and/or the second layer can include a tint instead of being entirely transparent. A typical transparent thermoplastic material suitable for use is polycarbonate. While polycarbonate is a preferred material, other transparent thermoplastic materials are also suitable.

A preferred lens includes a first film laminated to either the first layer and/or the second layer that filters the light transmitted through it. An example of such a film is a polarized film that permits only light waves aligned with the filter to be transmitted through the film; light waves not aligned with the polarized film, such as those that scatter and typically cause glare, are prevented from being transmitted through the film. When the lens is used with protective eyewear, such as goggles and safety glasses, the polarized film reduces the glare caused by light, in particular sunlight, reflecting off of snow and water. In so doing, the lens with the polarized filter allows the user to see more objects more clearly, increasing safety. In addition, reducing the glare of reflected light reduces eye-strain for the user and other associated ailments associated with eye strain, such as headaches. Furthermore, reducing glare diminishes the likelihood and/or the severity of temporary or permanent eye damage caused from burns and similar ailments that lead to snow-blindness.

In addition, a second film laminated to at least one of the first layer, the second layer, and the first film comprises a photochromatic film that automatically adjusts to vary the amount of light that is transmitted through the film in response to the amount of ultraviolet radiation received by the film. As one, non-limiting example, as the amount of ultraviolet radiation received by the photochromatic film increases, the photochromatic film becomes darker and thereby decreases the amount of visible light, which is typically proportional to the amount ultraviolet radiation received by the photochromatic film, that is transmitted through the photochromatic film. Conversely, when the amount of ultraviolet radiation received by the photochromatic film decreases, the photochromatic film becomes relatively less dark, or lighter, thereby increasing the amount of visible light that is transmitted through the photochromatic film. In each instance, the photochromatic film adjusts automatically to the prevailing visible light conditions, thereby enhancing what a user sees through the lens.

The photochromatic film optionally includes various tints or coloring agents that block selected wavelengths of light. As known, visible (white) light comprises a spectrum of colors at different wavelengths. Tinted or colored films selectively block certain wavelengths of light from being transmitted through the photochromatic film. In doing so, the remaining light transmitted through the photochromatic film enhances the contrast between objects. An example of selecting such a tint is the use of rose-gray or purple-gray, or a purple-rose-gray tint, that is selected to enhance the contrast between lighter and darker objects in low-light or flat-light conditions during cloudy or partly-cloudy days. For example, such tints enhance the contrast between uneven surfaces on snow while skiing, thereby allowing a user to see the uneven surface with sufficient time to react and, therefore, increasing the safety and the enjoyment of the user.

Another example of a tint suitable for use with the photochromatic film includes one that changes color in response to the received ultraviolet light, just as the photochromatic film increases or decreases in darkness (or grayness) when exposed to ultraviolet light. As a non-limiting example, the tint of the film may change from a yellow-gray to a rose-gray, rose-purple-gray, or purple-gray, when exposed to increasing amounts of ultraviolet radiation. By using a tint that adjusts to ultraviolet light, the range of visible light conditions in which the lens with the photochromatic film increases, thereby making the lens more adaptable to a variety of light conditions.

Embodiments of the lens disclosed herein are adapted for use with a frame that is configured to receive the lens and position the lens proximate a user's face and eyes. The frame includes various types of securing means to hold the frame about the user's head, such as, for example, arms, as in various safety glasses, straps like those used in ski goggles, and other methods of affixing goggles to the user's head. Other embodiments include a lens affixed in the form of a visor to headwear such as helmets used by military pilots and other occupations in which a lens that adapts to ambient or changing light conditions is desirable.

Methods of manufacturing various embodiments of the lens are disclosed herein, as well as various frames and other methods of positioning the lens proximate to a user's eyes are disclosed.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Summary does not contain all of the aspects and embodiments of the one or more present inventions, is not meant to be limiting or restrictive in any manner, and that the invention(s) as disclosed herein is/are and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

To further clarify the above and other advantages and features of the one or more present inventions, reference to specific embodiments thereof are illustrated in the appended drawings. The drawings depict only typical embodiments and are therefore not to be considered limiting. One or more embodiments will be described and explained with additional specificity and detail through the use of the accompanying drawings in which.

The drawings are not necessarily to scale.

DETAILED DESCRIPTION

Illustrated in FIGS. 2 through 7 are several views of an embodiment of a lens disclosed herein. In addition, FIG. 1 illustrates a cross-section A-A (not to scale) of the lens illustrated in FIGS. 2 through 7.

Figure 1:
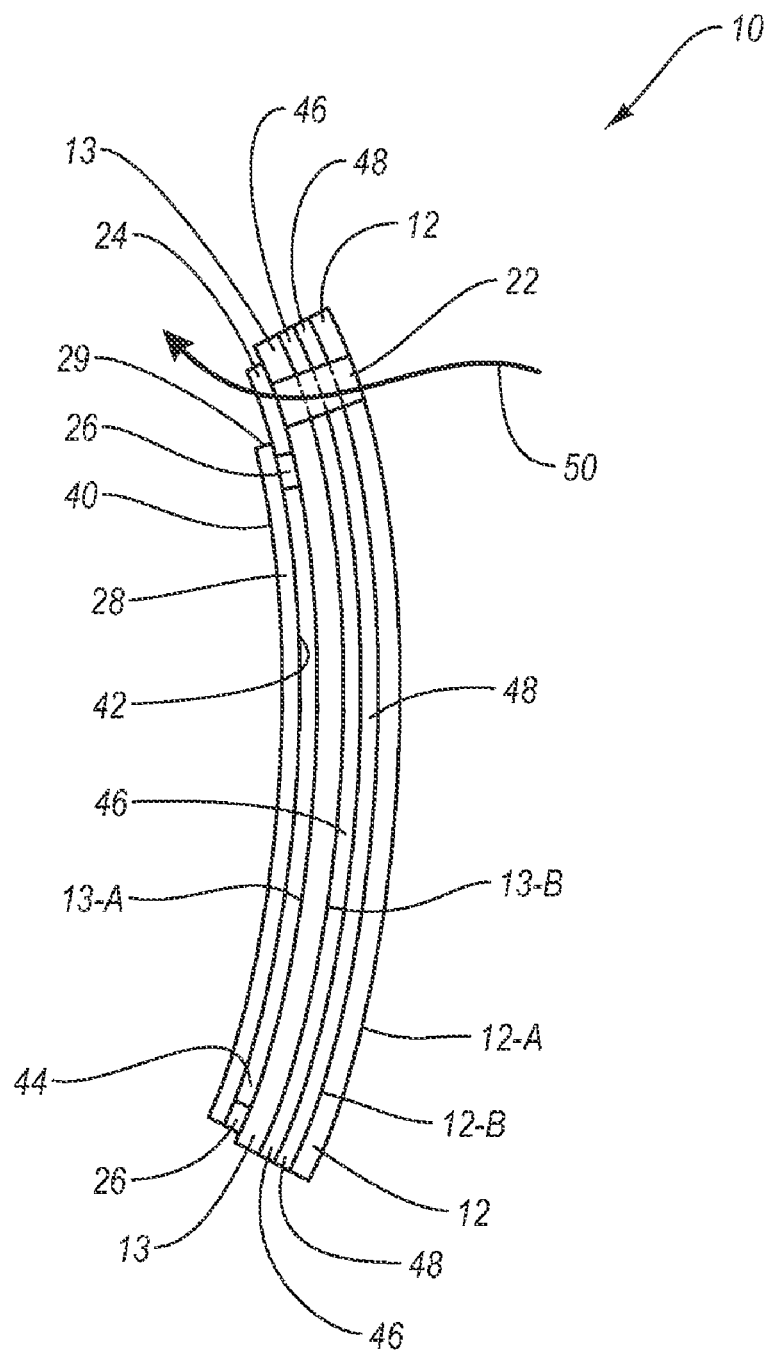
FIG. 1 a cross-section A-A of the lens in FIG. 2.

Turning first to FIG. 1, an embodiment of a lens 10 includes a first layer 12 made of a transparent thermoplastic material. One embodiment of the first layer includes a clear material, i.e., without tint; another embodiment includes a selected color of tint, which includes gray and/or other colors of the spectrum. The first layer 12 is the outer layer of the lens 10 that is exposed to the ambient environment. Optionally, the first layer 12 includes a scratch resistant coating (not shown) applied to the outer first surface 12-A. The first layer 12 also includes an inner first surface 12-B opposite the outer first surface 12-A.

The lens 10 also includes a second layer 13 made of a transparent thermoplastic material. An embodiment of the second lens includes a clear material, i.e., without tint; another embodiment includes a selected color of tint, which includes gray or other colors of the spectrum. The second layer 13 is the inner layer of the lens 10 that is proximate a user's eyes when the lens 10 is received by a frame that is positioned about the user's head. Like the first layer 12, the second layer 13 includes an outer second surface 13-A, but this outer second surface is positioned proximate the user's eyes instead of the ambient environment. The second layer 13 also includes an inner second surface 13-B.

The first layer 12 and the second layer 13 are typically made from a flat polycarbonate sheet. Other transparent thermoplastic materials that provide the desired characteristics as described below will also work. As will be discussed below, the sheet is thermoformed to have a curvature along both a long axis and a short axis to provide a spherical lens, thereby reducing distortion of the light that is transmitted through the lens and, to a degree, increasing clarity and visual acuity of objects that a user views through the lens.

A first film or layer 48 is affixed to first layer 12. While the first film 48 is shown affixed to the inner first surface 12-B of the first layer 12, it is optionally affixed to the inner second surface 13-B of the second layer 13. The first film 48 is a transparent, polarized film, i.e., a film that is selected and configured to filter and permit those wavelengths of light oriented in the same direction as the filter in the polarized film to be transmitted through the first film 48. As a non-limiting example, if the polarizing filter in the first film 48 is oriented towards the horizontal, i.e., parallel to a user's eyes, only those wavelengths of light oriented in the same direction (horizontal) will pass through the first film; wavelengths of light oriented in any direction other than horizontal (such as vertical or at a diagonal to the horizontal filter) will be blocked by the first film 48. It will be understood, of course, that the orientation of the filter direction of the first film 48 can be selected to a desired orientation. An advantage that polarized films, such as first film 48, provide is that they significantly reduce glare from the light reflected off various objects. This is particularly significant for those objects that typically are highly reflective, including, but not limited to, snow, water, glass, chrome, metals, and other similar color and types of objects. When a user views an object through a polarized film, the polarized film reduces the glare caused by reflected light off of that object, thereby allowing the user to more easily view the object and other objects near the reflective object. In reducing glare, eye strain that a user endures may be reduced for the user as well as other associated ailments associated with eye strain, such as headaches. Furthermore, reducing glare diminishes the likelihood and/or the severity of temporary or permanent eye damage caused from burns and similar ailments that lead to snow-blindness.

Figure 7:
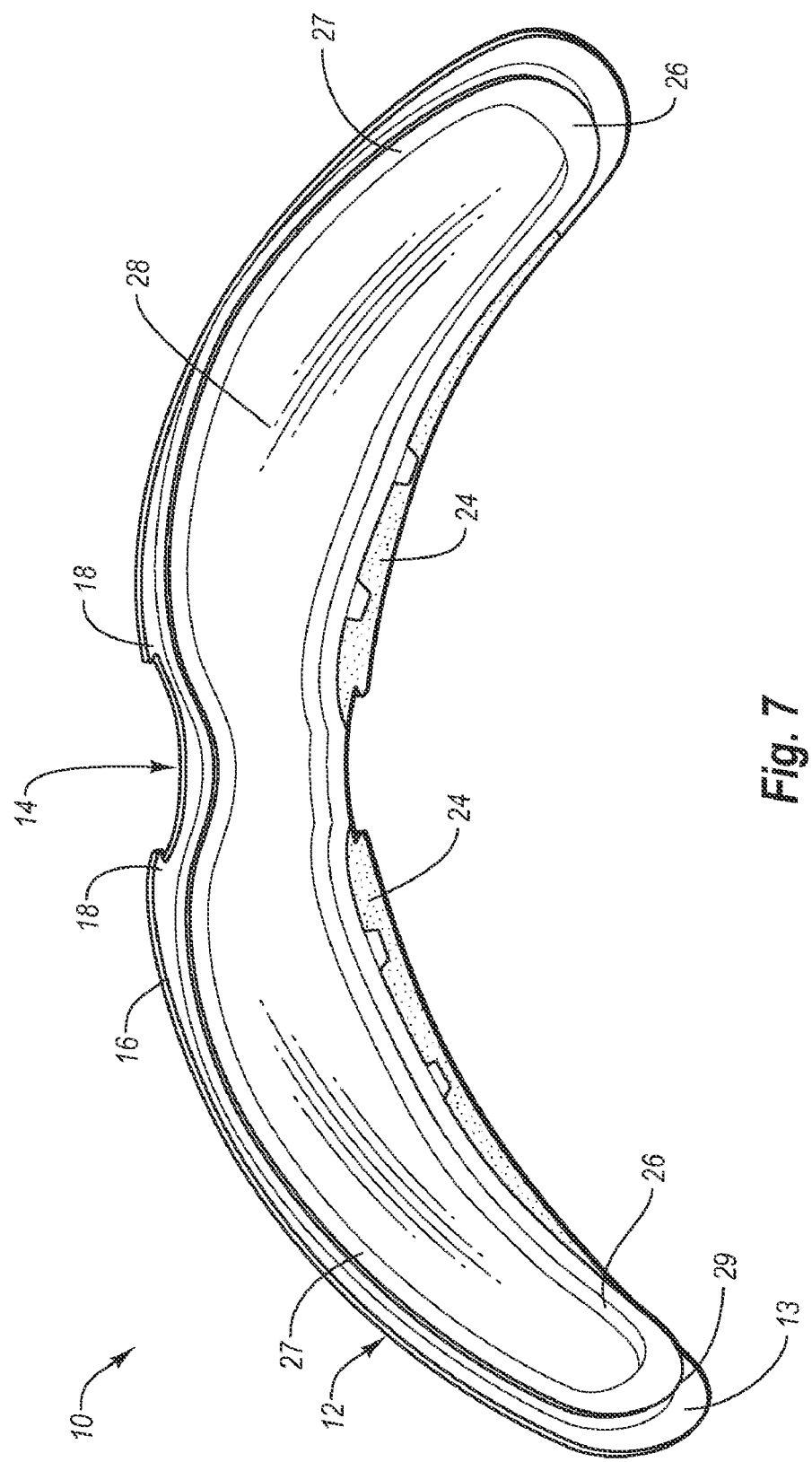
FIG. 7 is a bottom-view of the lens in FIG. 2.

The lens 10 also includes a transparent second film, a photochromatic film 46. In FIG. 7, the photochromatic film 46 is affixed to the inner second surface 13-B of the second layer 13 and the first film 48, but it is understood that the photochromatic film 46 can alternatively be affixed to the inner first surface 12-B of the first layer 12 with the first film 48 affixed to the inner second surface 13-B of the second layer 13. The photochromatic layer 46 automatically adjusts to vary the amount of light that is transmitted through the photochromatic film 46 in response to the amount of ultraviolet radiation received by the photochromatic film 46. As one, non-limiting example, as the amount of ultraviolet radiation received by the photochromatic film 46 increases, the photochromatic film 46 becomes darker and thereby decreases the amount of visible light, which is typically proportional to the amount of ultraviolet radiation received by the photochromatic film 46, that is transmitted through the photochromatic film 46. Conversely, when the amount of ultraviolet radiation received by the photochromatic film 46 decreases, the photochromatic film 46 becomes relatively less dark, or lighter, thereby increasing the amount of visible light that is transmitted through the photochromatic film 46. In each instance, the photochromatic film adjusts automatically to the prevailing visible light conditions, thereby enhancing what a user sees through the lens 10.

The photochromatic film 46 optionally includes various tints or coloring agents that block selected wavelengths of light. As known, visible (white) light comprises a spectrum of colors at different wavelengths. Tinted or colored films selectively block certain wavelengths of light from being transmitted through the photochromatic film 46. In doing so, the remaining light transmitted through the photochromatic film 46 enhances the contrast between objects. An example of selecting such a tint is the use of rose-gray or purple-gray, or a purple-rose-gray tint, that is selected to enhance the contrast between lighter and darker objects in low-light or flat-light conditions during cloudy or partly-cloudy days. Of course, tints and coloring agents of other colors within the spectrum of available colors can be selected, including, but not limited to, red; red-orange; persimmon; yellow; blue; green; and others. For example, such tints enhance the contrast between uneven surfaces on snow while skiing, thereby allowing a user to see the uneven surface with sufficient time to react and, therefore, increasing the safety and the enjoyment of the user.

Another example of a tint suitable for use with the photochromatic film 46 includes one that changes color in response to the received ultraviolet light, just as the photochromatic film 46 increases or decreases in darkness (or grayness) when exposed to ultraviolet light. As a non-limiting example, the tint of the photochromatic film 46 may change from a yellow-gray to a rose-gray, rose-purple-gray, and/or purple-gray, when exposed to increasing amounts of ultraviolet radiation. Of course, different combinations of tints that adjust to ultraviolet can be used, including those within the spectrum of available colors, such as red; red-orange; persimmon; yellow; blue; green; and others. By using a tint that adjusts in color to ultraviolet light, the range of visible light conditions in which the lens with the photochromatic film 46 increases, thereby making the lens more adaptable to a variety of light conditions.

As an example, a lens 10 that includes the polarized film 48 and the photochromatic film 46 tinted with a rose-purple-gray color adjusts to the ambient light conditions in response to the amount of ultraviolet light received at that photochromatic film 46 and thereby allows varying amounts of visible light to be transmitted through the lens 10. For instance, in very bright sunlight, such as a cloudless day, the photochromatic film 46 would be very dark in response to the large amount of ultraviolet radiation received at the photochromatic film 46. Combined, the polarized film 48 and photochromatic film 46 allow only from about 6% to about 20% and, more preferably, about 10% to about 16%, of the available ambient light to pass through the lens 10 in bright ambient light conditions.

Conversely, on a very cloudy day or late in the afternoon or early evening while the sun is setting, the ambient light conditions would be very low and, consequently, the amount of ultraviolet radiation received at the photochromatic film 46 would be very low. As a result, the photochromatic film 46 would be relatively less dark and, consequently, allow a relatively larger amount of ambient light to pass through the photochromatic film 46. In this example, the polarized film 48 and the photochromatic film 46 combine to permit about 26% to about 40% and, more preferably, about 30% to about 36% of available ambient light to pass through the lens 10 in relatively low ambient light conditions.

Thus, as this example illustrates, an embodiment of the lens 10 allows about 6% to about 40% and, more preferably, about 10% to about 36% of the available ambient light to pass through the lens depending on the ambient light conditions and the ultraviolet light that reaches the photochromatic film layer 46. As it will be understood, any amount of ambient light between the top and bottom of these ranges will be transmitted through the lens 10 depending on the amount of ultraviolet radiation received at the photochromatic film 46. Another example of the lens 10 includes the polarized film 48 and the photochromatic film 46 having a tint that changes color in addition to adjusting its relative darkness in response to the amount of ultraviolet radiation that reaches the photochromatic film 46. For example, in the very bright sunlight conditions described above, the tint optionally is a rose-purple-gray that allows, in combination with the polarized film 48, only allow from about 6% to about 20% and, more preferably, about 10% to about 16%, of the available ambient light to pass through the lens 10 in bright ambient light conditions.

In contrast, in low-light conditions such as a cloudy day or a late afternoon or evening, the photochromatic film 46 would receive relatively little ultraviolet radiation. Not only would the photochromatic film 46 become relatively less dark and allow more light to pass through the lens 10, the tint would also change color, from rose-purple-gray in bright ambient light conditions to a yellow-gray in low ambient light conditions. In other words, the different color tint would block a different wavelength of light. Because the wavelength of available light changes with the amount of ambient light—most notably, shorter wavelength blue light become more prevalent in the late afternoon and early evening, a tint that adjusts color to the ambient light conditions would increase the contrast between objects as viewed through the lens 10 by a user. In this instance, the yellow-gray tint of the photochromatic lens 46 would allow from about 33% to about 47% and, more preferably, from about 37% to about 43% of available ambient light to pass through the lens 10 in relatively low ambient light conditions.

Thus, as this example illustrates, this embodiment of the lens 10 allows about 6% to about 47% and, more preferably, about 10% to about 43% of the available ambient light to pass through the lens depending on the ambient light conditions and the amount of ultraviolet radiation that reaches the photochromatic film layer 46. As it will be understood, any amount of ambient light between the top and bottom of these ranges will be transmitted through the lens 10 depending on the amount of ultraviolet radiation received at the photochromatic film 46. This embodiment therefore provides an optimum range of light to be transmitted through the lens 10 over a wider range of light conditions than the previous example. In addition, it will be understood that the adaptable tint can be selected for a variety of colors and light conditions, not just those recited in these examples. Of course, different combinations of tints that adjust to ultraviolet radiation can be used, including those within the spectrum of available colors, such as red; red-orange; persimmon; yellow; blue; green; and others.

Another embodiment of the lens includes a photochromatic dye applied to a surface of at least one of the first layer and the second layer to form an equivalent of a film on the surface of the first layer and/or the second layer. Alternatively, the photochromatic dye can be incorporated into the material of at least one of the first layer and the second layer. The photochromatic dye optionally includes a tint of the desired type as described above.

A lens of the types described above is manufactured as follows. The first layer 12 and the second layer 13 are made from a transparent thermoplastic resin, such as polycarbonate, that is extruded in a flat sheet. The polarized film 48 has a bonding agent or chemical fixant applied to one or both sides of the polarized film 48. Conversely, the bonding agent or chemical fixant (not shown) can be applied to one or both of the inner first surface 12-B of the first layer 12 and the inner second surface 13-B of the second layer 13. Of course, the bonding agent can also be applied to both the polarized film 48 and the first layer 12 and the second layer 13. The bonding agent can by any type of transparent bonding agent known in the art that can be used to adhere the polarized film 48 to the first layer 12, including, but not limited to, UV cured, heat cured, pressure cured, and typical time/air cured bonding agents. The result is that the polarized film 48 forms a laminate with the first layer 12.

The photochromatic film 46 is applied in the same manner as the polarized film 48 to the first layer 12, the polarized film 48, and the second layer 13. In other words, the same bonding agent as that used with the polarized film 48 is applied to one or more of the photochromatic film 46, polarized film 48, first layer 12, and second layer 13 so that the photochromatic film 46 forms a laminate with the polarized film 48 and the first layer 12.

The second layer 13 is then affixed to the laminate of the photochromatic film 48, polarized film 46, and first layer 12 to form a flat lens 10. It will be understood that the order in which the various films and layers are joined to form the laminated lens 10 can be varied as desired. Further, the bonding agent of all the layers can be activated at the same time once each of the polarized film 46, photochromatic film 48, first layer 12, and second layer 13 are laminated to each other, or the bonding agent can be activated in sequence as each of the aforementioned is applied. Finally, the bonding agent can be applied to the entire surface of each of the aforementioned elements or it may be applied to selected portions only of the polarized film 48, the photochromatic film 46, and the first and second layers 12, 13, respectively.

In applying the polarized film 48 and the photochromatic film 46, care must be taken to avoid introducing lines, wrinkles, air bubbles, and other defects into the laminated lens 10. The polarized film 48 and photochromatic film 46 should provide a smooth surface substantially free of such defects within the tolerance level associated with the manufacturing process.

The flat laminated lens 10 is then placed into a mold of a selected shape and thermoformed at a selected pressure and temperature to provide the desired shape and curvature. For example, an embodiment of the lens 10 can be formed as a large, single lens with dimensions of from about 185 millimeters to about 235 millimeters in width and, more preferably, from about 195 millimeters to about 225 millimeters, corresponding to the horizontal axis 36 illustrated in FIGS. 2 and 3. The embodiment of the lens 10 has a height of from about 80 millimeters to about 130 millimeters and, more preferably, from about 90 millimeters to about 120 millimeters, corresponding to the vertical axis 30 illustrated in FIGS. 2 and 3. The lens 10 has a thickness of from about 0.4 millimeters to about 2.0 millimeters and, more preferably, from about 0.6 millimeters to about 1.8 millimeters.

Figure 2:
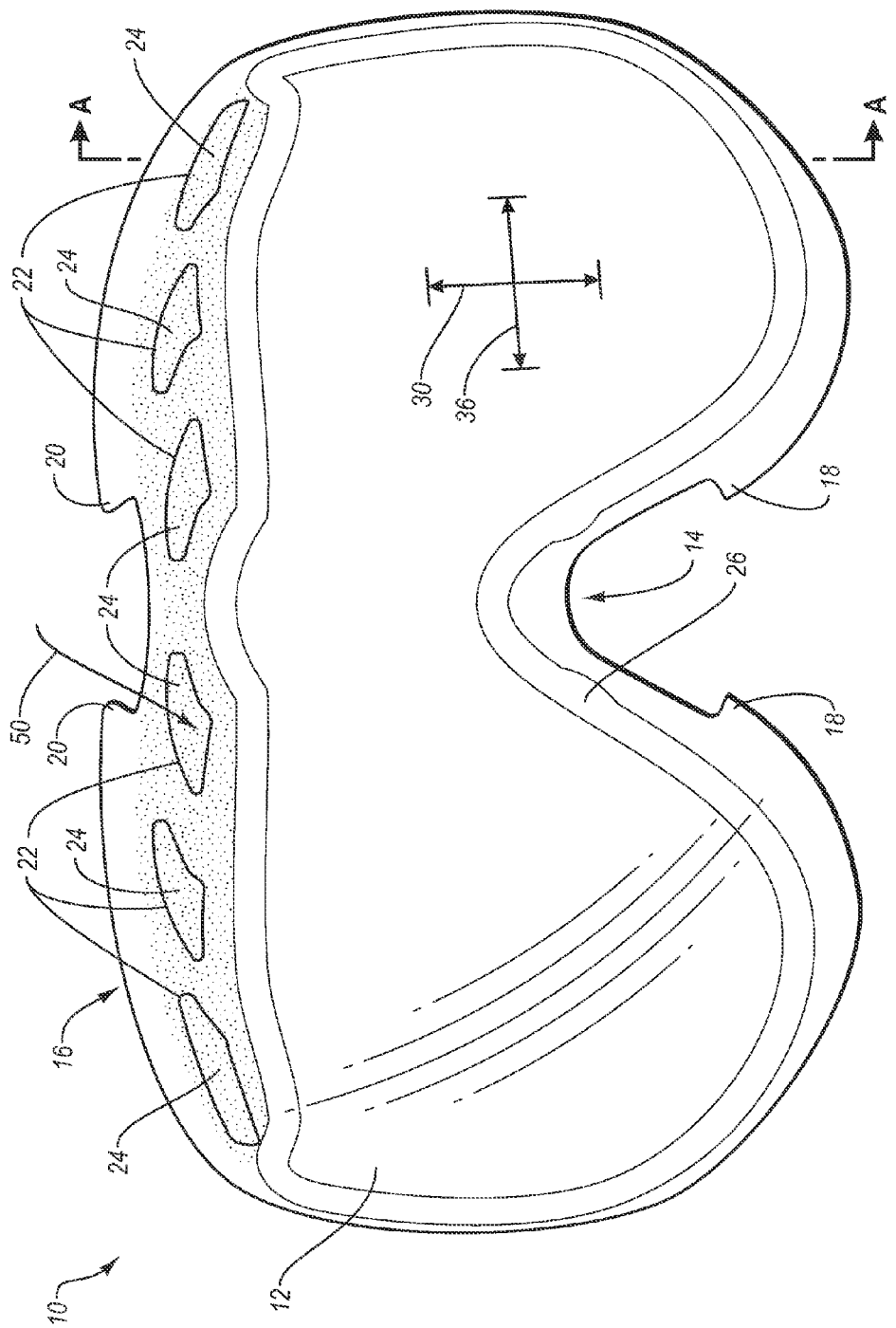
FIG. 2 is front-view of an embodiment of a lens disclosed herein.
Figure 3:
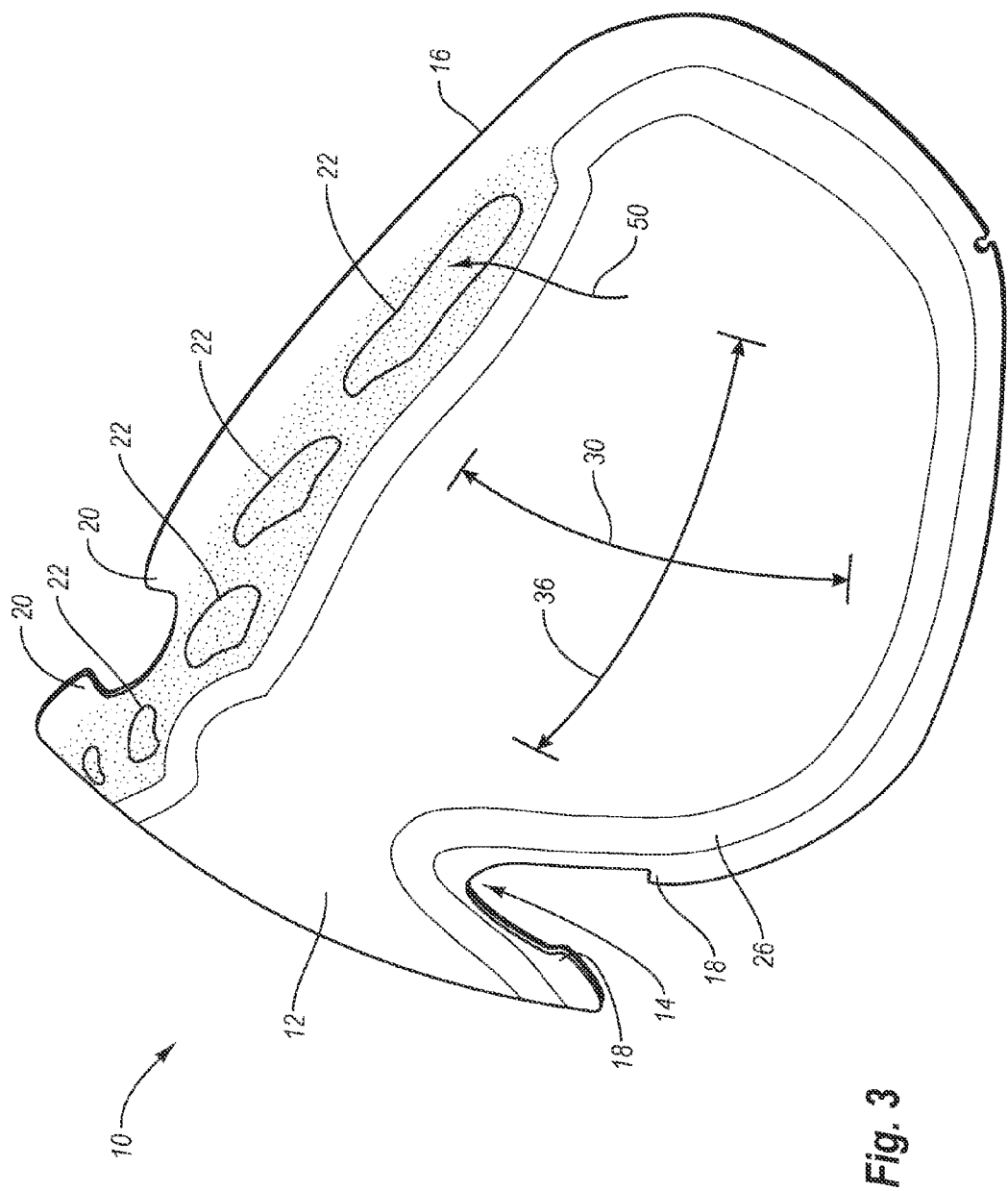
FIG. 3 is a front iso-view of the lens in FIG. 2.

The flat laminated lens 10 is selectively provided with an arcuate shape or curvature in one or both of the vertical axis 30 and the horizontal axis 36 illustrated in FIGS. 2 and 3. The minor, or vertical axis 30, extends from the forehead downward toward the user's cheeks, while the major, horizontal axis 36, extends generally from one side to the other side of the user's head in alignment with the user's eyes. A lens 10 that includes a arcuate shape or curve is desirable because the curve, especially a curve that is similar to the natural curve of the human eye, can increase visual acuity and clarity by minimizing the distortion of light that may occur as it passes through a flat lens.

Typically, a curve is described as having either a radius of curvature or a given base curve number, which has a numerical relation to the radius of curvature. Specifically, the base curve number is calculated by dividing the radius of curvature in millimeters into 530.

The radius of curvature in either the horizontal axis 36 and the vertical axis 30 extends in a range of from about 44 millimeters to about 265 millimeters, which qualitatively corresponds to a significant curve to a nearly flat, or insignificant curve, and corresponds to a base curve of from about 12 to about 2. More preferably, the curve in the horizontal axis 36 ranges from about a 3 base curve to about a 9 base curve and, more preferable still, from about a 5 base curve to about a 7 base curve. The curve in the vertical axis preferably ranges from about a 1 base curve to about a 7 base curve and, more preferable still, from about a 3 base curve to about a 5 base curve. Of course, it will be understood that the curve in either of both of the horizontal axis 36 and the vertical axis 30 need not be constant across the entire width or height of the lens 10 and, in fact, can vary across the width and the height of the lens 10 as desired.

As mentioned, the flat lens 10 comprised of the first layer 12, the polarized film 48, the photochromatic film 46, and the second layer 13 is thermoformed as a single piece in a mold of a selected shape at a selected pressure and temperature to create an arcuate shape of a selected curvature. Because the mold provides a curved or arcuate shape, the process is carefully controlled to minimize or eliminate any visible stretching, wrinkling, cracking or crackling, lines, or other distortions in either or both the polarized film 48 and the photochromatic film 46 as pressure is applied and the polarized film 48 and photochromatic film 46 with the first layer 12 and the second layer 13 each increase in length as the lens 10 assumes a curved shape under the heat and pressure of the mold. Such a thermoforming process allows a high quality, relatively thinner and more flexible lens 10 to be produced at less cost and complexity than the typical injection molding process normally used to create a curved lens.

The result is a thin lens 10, thinner than a lens typically formed through injection molding, that has less weight and greater flexibility. The flexibility of the lens 10 allows a user to easily remove and replace the lens 10 in a frame, as will be described below. In addition, the flexible lens 10 is resistant to breaking under impacts and other sudden forces unlike more rigid and thicker lenses. Further, the light weight of the lens relative to other lenses creates a more comfortable wearing experience for the user, with less weight, pinching, and sliding of the frame and lens around the user's nose and head, an important factor when worn for extended periods or in cold and/or inclement weather. It should be noted that the lens 10 retains its flexibility in a wide range of temperature conditions, including all those that it might normally be exposed to, such as from about −30 degrees Fahrenheit to about 120 degrees Fahrenheit.

Another embodiment of the lens includes those that are formed by having at least one of the first layer and the second layer formed by injection molding and/or casting to the desired shape and/or curvature rather than thermoforming a flat first layer and flat second layer. The polarized film and/or the photochromic film can be applied as a laminate as described above to at least one of the injection molded or cast first layer and the second layer.

Examples of the above described lens are manufactured according to instructions from Zeal Optics, Inc., 4843 Pearl Street 1A, Boulder, Colo., 80301 by Mitsubishi Chemical Corporation, 14-1 Shiba 4-chome, Minato-ku, 108-0014, Tokyo, Japan.

Optional elements of the lens are further illustrated in FIG. 1. For example, the lens 10 can include one or more vents 22, also illustrated in FIGS. 2 through 7, that allow venting air illustrated as flow arrow 50 to pass through the lens 10 from an exterior of the lens 10 into an interior portion 140 of the frame 124 (illustrated in FIGS. 10 and 11). A porous foam 24 can be affixed with a bonding agent as known in the art to the outer surface 13-B of the second layer 13 and proximate to the vent 24. The porous foam 24 allows venting air 50 to pass through the vent(s) 22, while at the same time preventing or limiting the entrance of dust, snow, dirt, other particulate matter, and the like from entering into the interior space 140 of the frame 124 through the vent(s) 22. The venting air 50 passes through the porous foam 24, thereby being slowed and dispersed by the foam in the interior space 140. The venting air 50 acts to prevent and/or minimize any condensation that might otherwise buildup in the interior space 140 of the frame 124.

Figure 8:
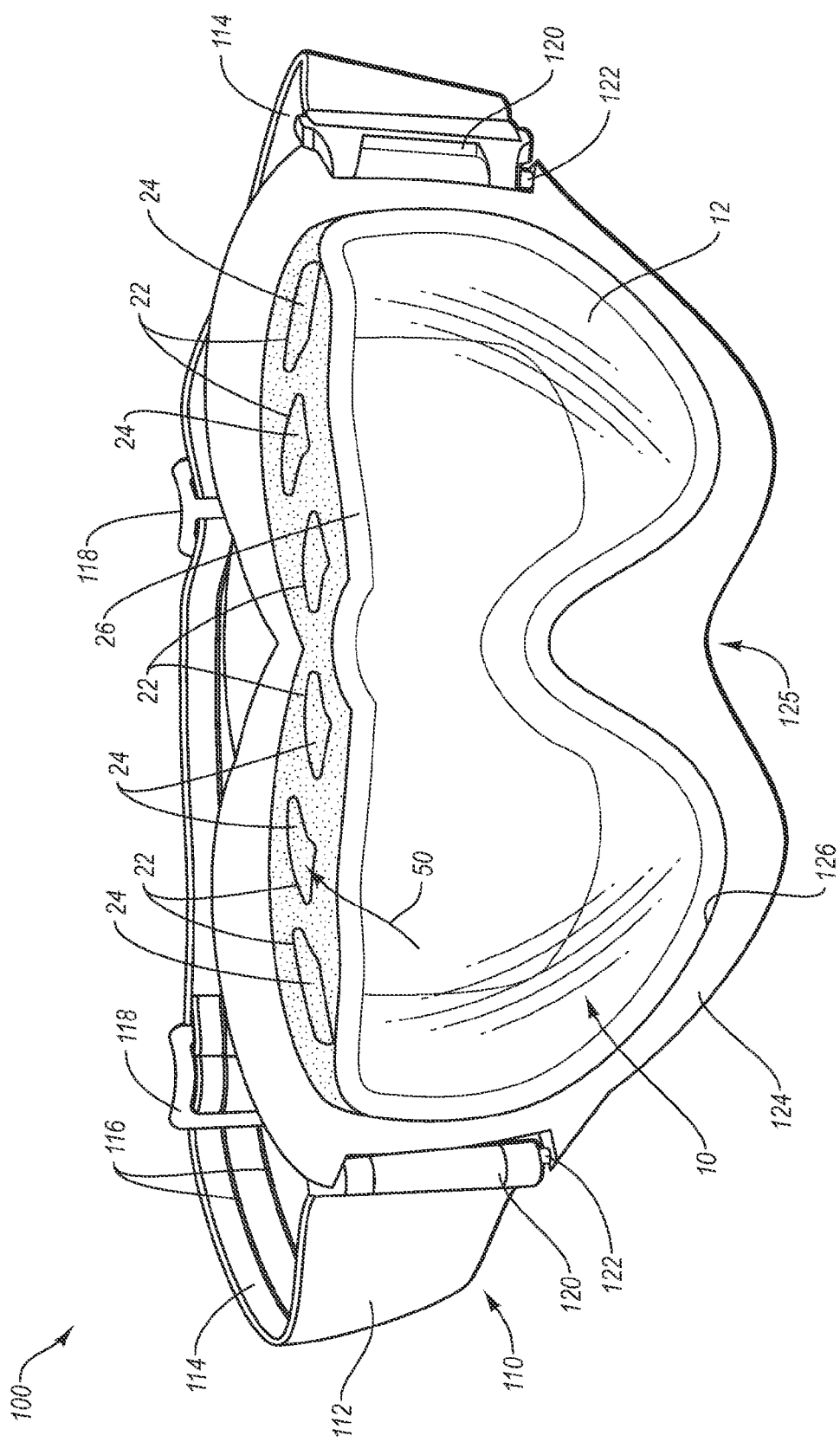
FIG. 8 is a front-view of an embodiment of a frame configured to receive the lens in FIG. 2.
Figure 9:
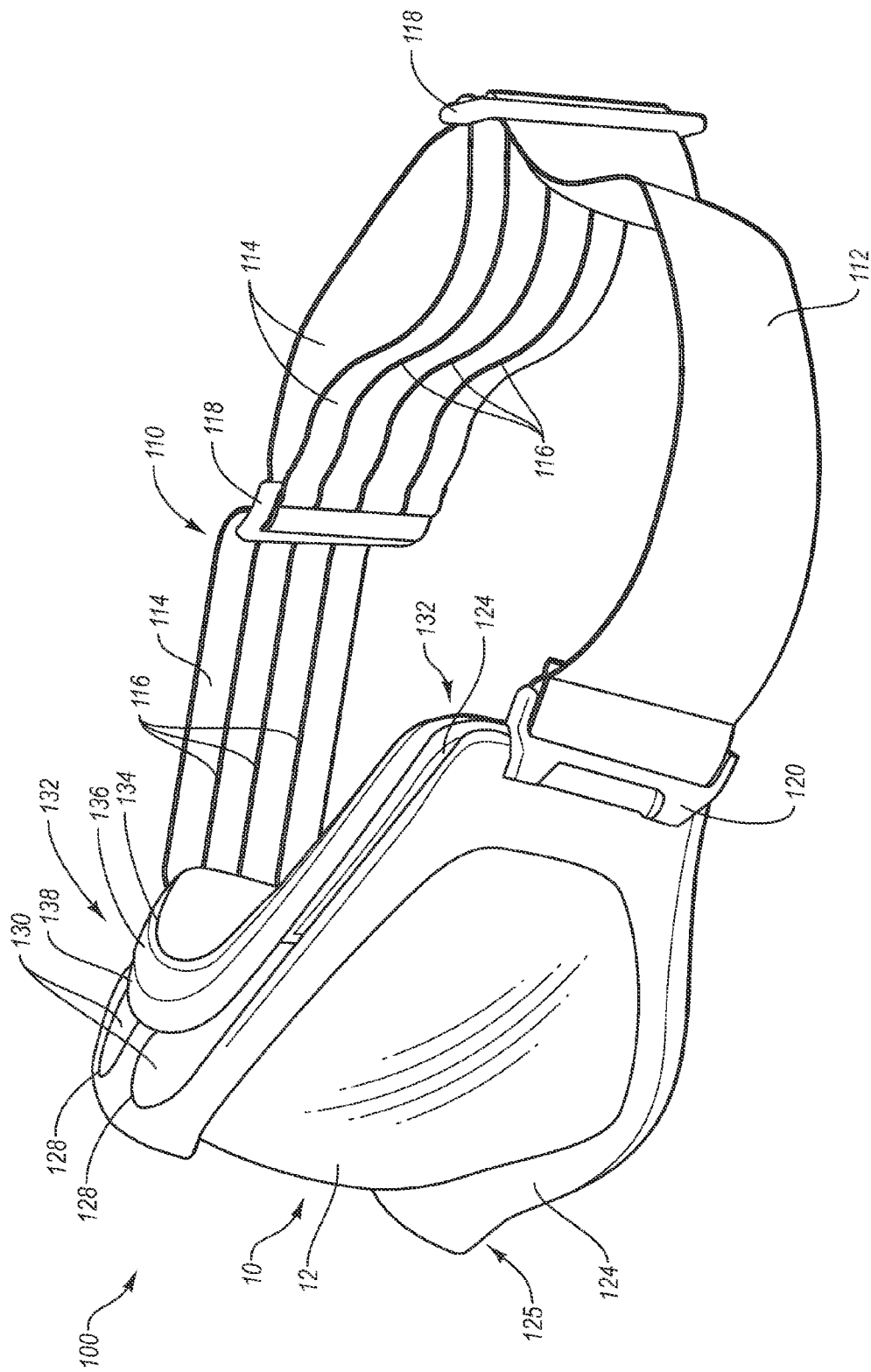
FIG. 9 is a side-view of the frame and lens in FIG. 8.
Figure 10:
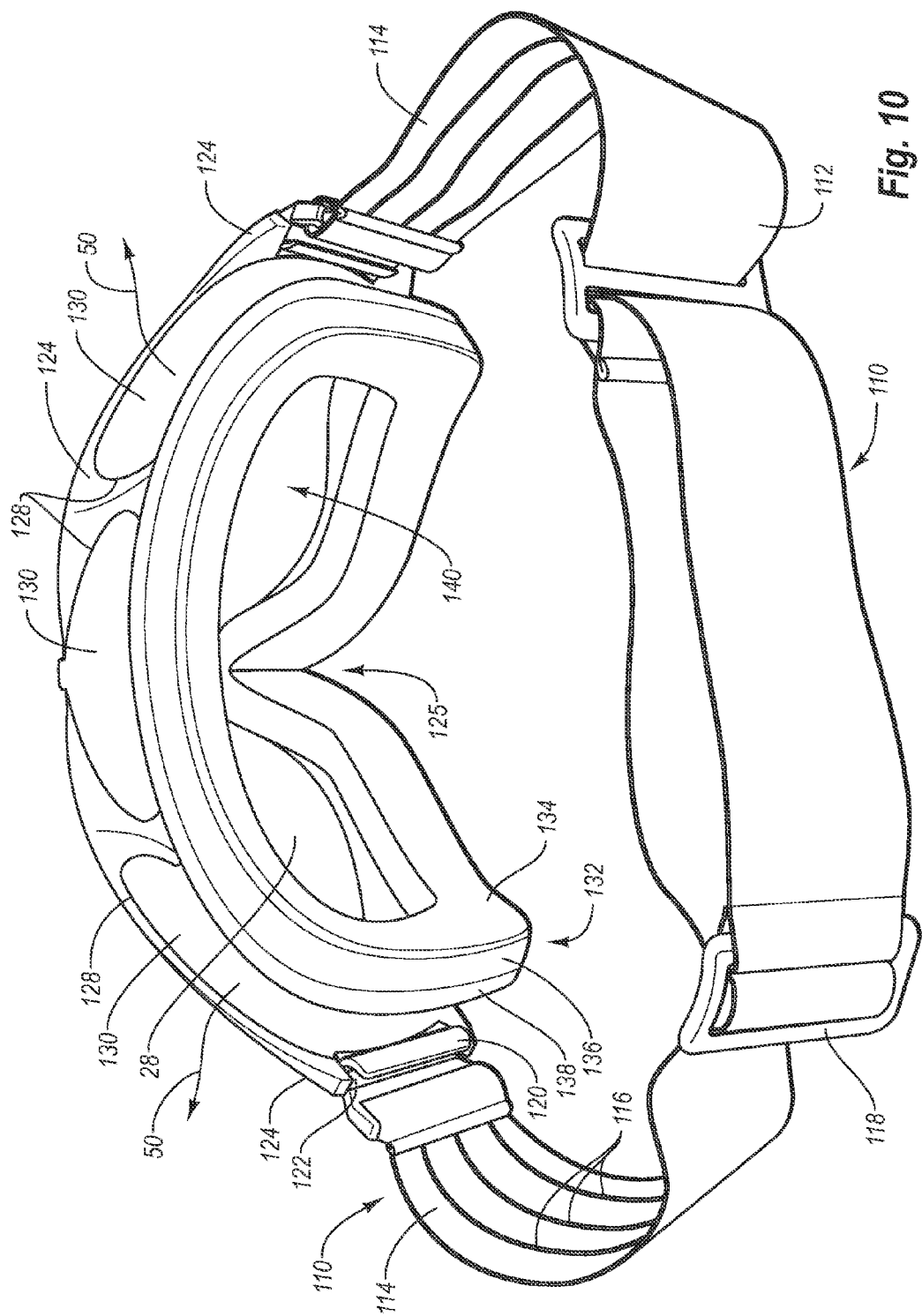
FIG. 10 is a top/rear-view of the frame and lens in FIG. 8.
Figure 11:
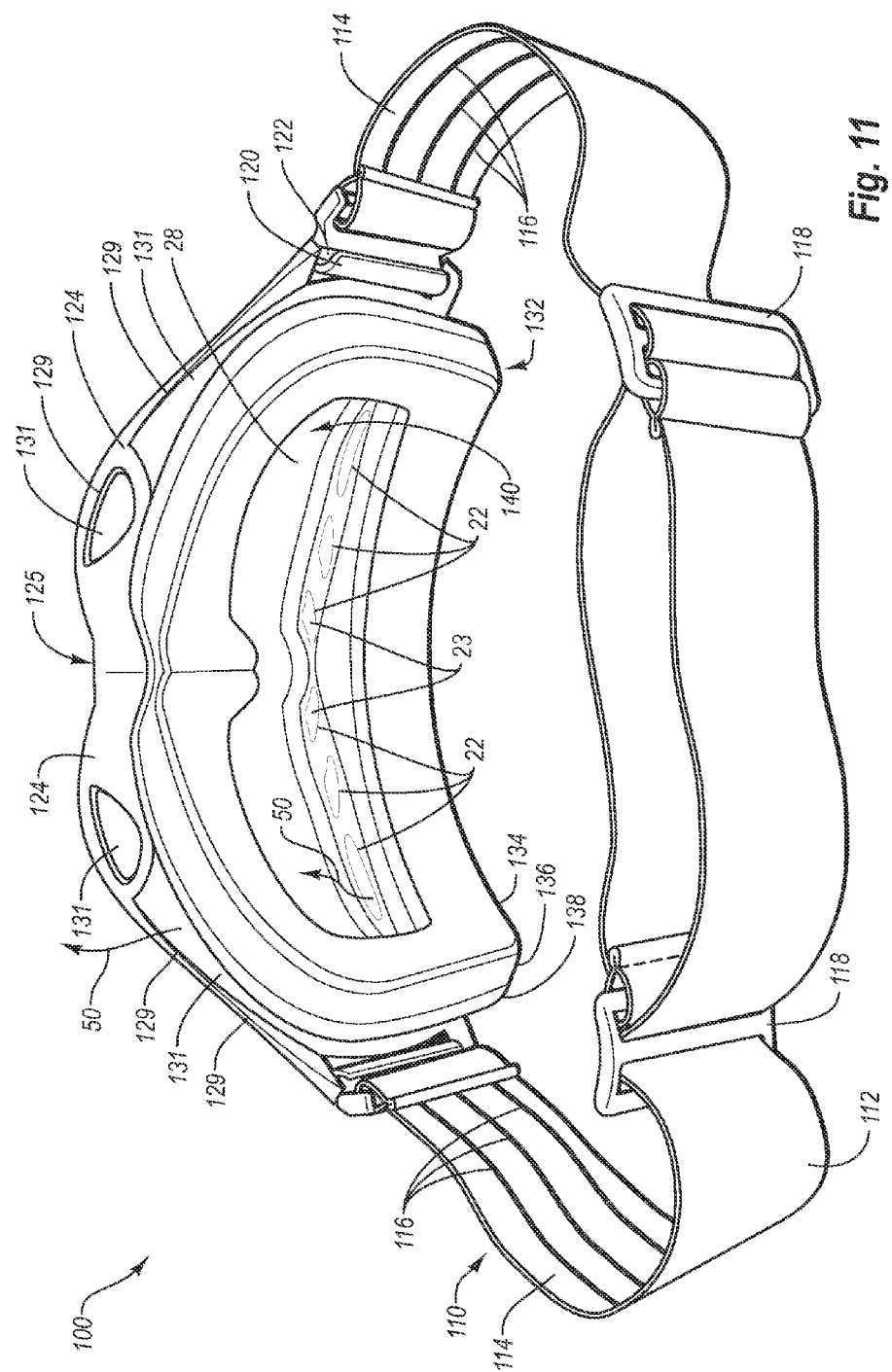
FIG. 11 is a bottom/rear-view of the frame and lens in FIG. 8.

The venting air 50 passes through the interior space 140, at least partially replacing the air therein and aiding the evaporation of any condensation in the interior space 140, such as condensation that might otherwise form on the interior of the lens 10. A portion of the venting air 50 then passes through a porous upper frame vent foam 130 and out the upper frame vent 128 to the exterior of the frame 124. Similarly, a portion of the venting air 50 passes through a porous lower frame vent foam 131 and out the lower frame vent 129 to the exterior of the frame 124. This process is best illustrated in FIGS. 8, 10, and 11. The upper frame vent foam 130 and lower frame vent foam 131 allow venting air 50 to pass through the upper frame vent 128 and lower frame vent 129, while at the same time preventing or limiting the entrance of dust, snow, dirt, other particulate matter, and the like from entering into the interior space 140 of the frame 124 through the upper frame vent 128 and the lower frame vent 129.

The lens 10 also optionally includes an anti-fog lens 28 spaced apart from the lens 10, in particular spaced apart from the second outer surface 13-A of the second layer 13, to form an air space 44 between the anti-fog lens 28 and the lens 10. Thermal gasket seals 26, such as those made from elastomers, polymers, and other similar, non-porous materials, are bonded to the anti-fog lens 28 and the second outer surface 13-A of the second layer 13 with a bonding agent, double sided tape, and other similar methods known in the art. The thermal gasket seals 26 limits or prevents the entrance of external air into the air space 44.

The air space 44 creates a thermal barrier between the lens 10, which often is exposed to inclement weather such as below freezing temperatures at the first outer surface 12-A of the first layer 12. In so doing, the air space 44 decreases the potential for condensation, such as sweat and water vapor present in the interior space 140 near a user's face from cooling and condensing on the anti-fog lens 28 or the second outer surface 13-A of the second layer 13. An anti-fog coating can optionally be applied to the anti-fog lens 28 to improve the anti-fogging characteristics of the anti-fog lens 28.

The anti-fog lens 28 is typically formed of a flat, transparent thermoplastic, such as one of acetate, polycellulose acetate, cellulose acetate, cellulose acetobutyrate, and a cellulose acetopropionate. The anti-fog lens 28 should have the characteristic of being light in weight and flexible so that when it is affixed via the thermal gasket seals 28 to the lens 10, the lens 10 retains its overall flexibility and relatively light weight to allow comfortable wear and its ability to be replaceable.

Other optional features of the lens 10 are better illustrated in FIGS. 2 through 7. For example, the embodiment of the lens 10 illustrated in FIGS. 2 through 7 includes a lens edge 16 configured to register with a groove 126 in the frame 124 so that the lens 10 is retained in the frame 124. The lens 10 includes nose tabs 18 and forehead tabs 20 along the lens edge 16 that are configured to register with structures in the frame 124 to increase the ability of the frame 124 to retain the lens 10 throughout a variety of conditions and environments, including potentially sudden and/or violent movements and impacts. The lens 10 also includes a nose portion 14 configured to register with the nose portion 125 of the frame 124 as well as a user's nose.

Figure 4:
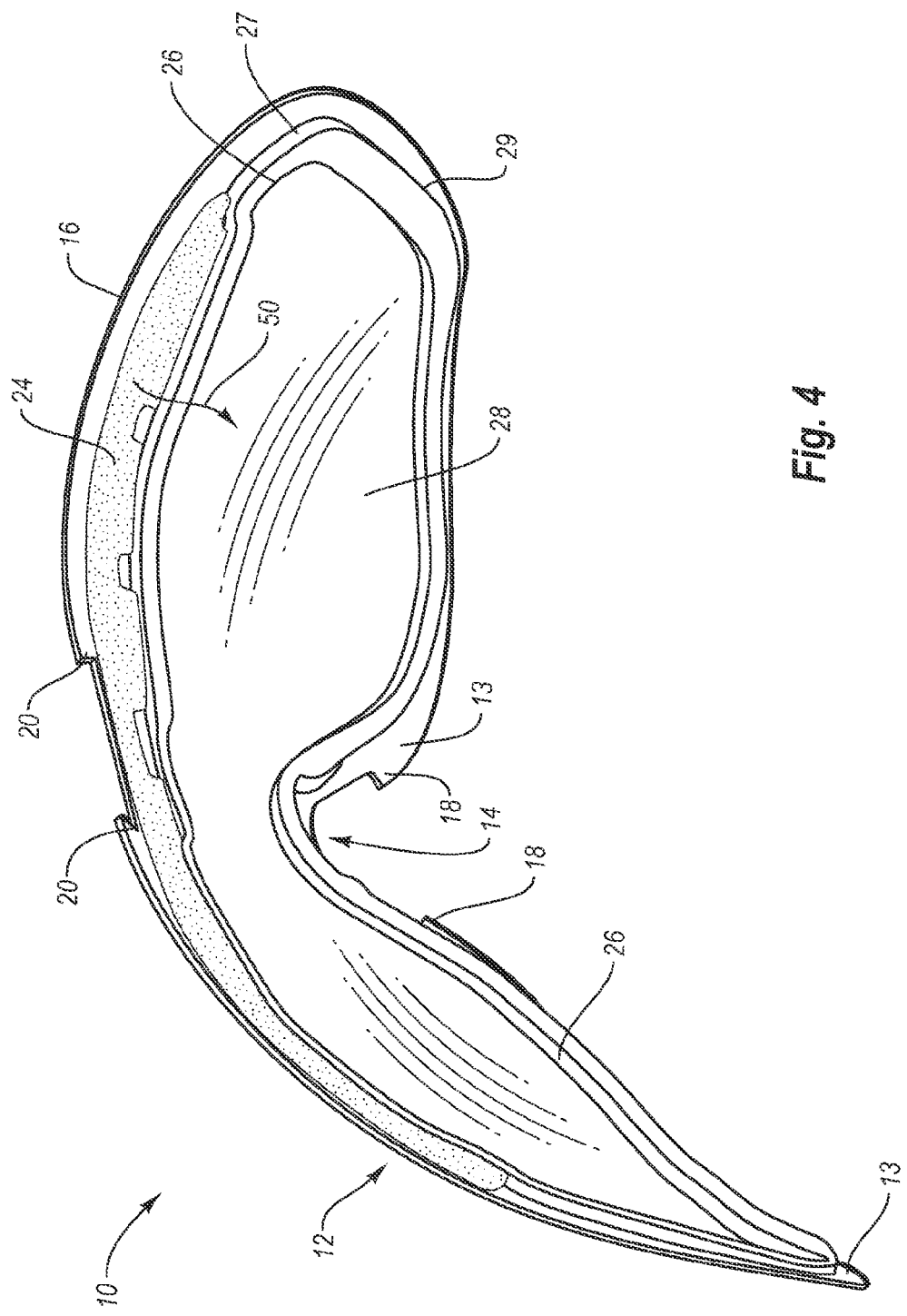
FIG. 4 is a rear iso-view of the lens in FIG. 2.
Figure 5:
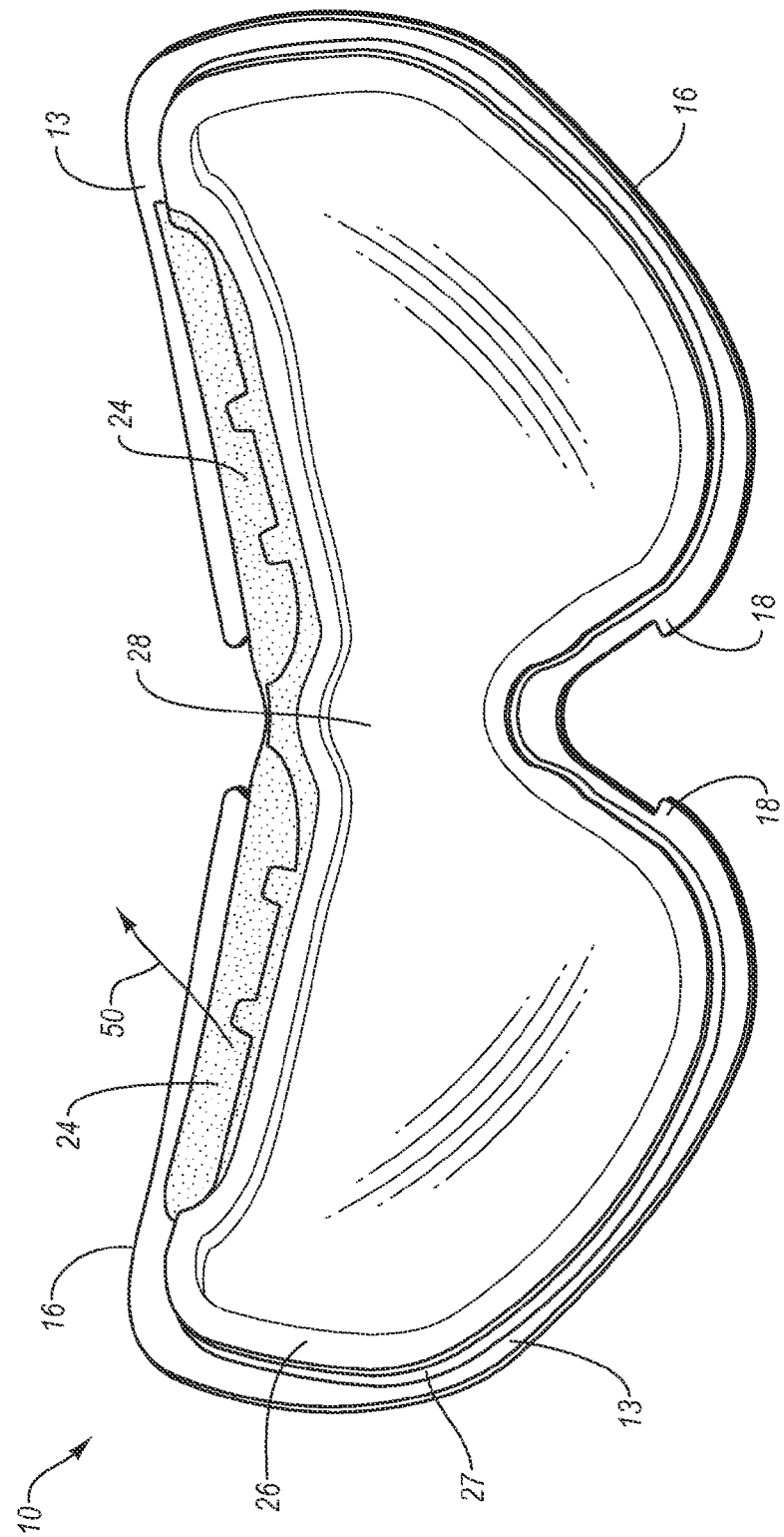
FIG. 5 is a rear-view of the lens in FIG. 2.
Figure 6:
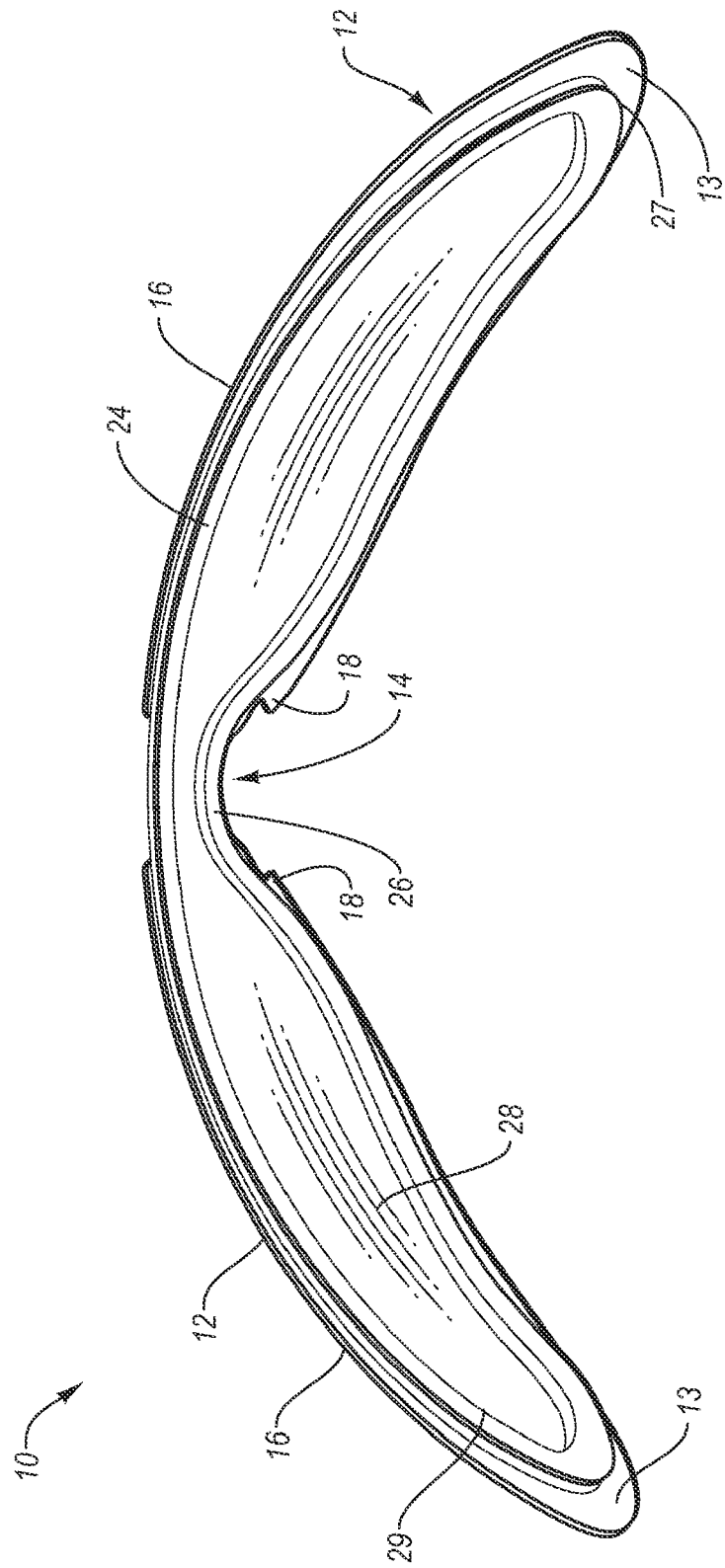
FIG. 6 is a top-view of the lens in FIG. 2.

As best seen in FIG. 4, the anti-fog lens 28 has an anti-fog lens edge 29 that registers with the thermal gasket seal edge 27.

In the embodiment of the lens 10 illustrated, the lens 10 includes a plurality of vents 22 across an upper portion of the lens 10. The vents 22 can be of a variety of shapes and sizes and therefore are not limited to the shapes and sizes illustrated. A single, continuous strip of porous foam 24 is affixed to the second outer surface 13-A of the second layer 13 that covers each of the plurality of vents 22. While a single, continuous strip of porous foam 24 is illustrated, a plurality of separate porous foam pieces or strips 24 to cover the vents 22 falls within the scope of the disclosure.

An embodiment of a goggle 100 that includes a frame 124 configured to retain and position the lens 10 about a user's head and proximate the user's eyes is illustrated in FIGS. 8 through 11. The frame 124 is made from a flexible thermoplastic, such as molded polyurethane, that allows the frame 124 to flex around a user's face to better create a seal against the user's face to prevent ambient environmental factors, such as dust, wind, cold, and snow from easily entering the interior space 140. The frame portion optionally includes a nose portion 125 that allows the frame 124 to rest upon the bridge of the user's nose.

The terms goggle, goggles, and pair of goggles are used here synonymously to refer to a structure that has a frame sized to hold and configure to position a transparent lens, with or without tint, in front of the user's eyes to offer protection of some type to the user's eyes. While some goggle, goggles, and/or pair of goggles may have two separate lenses, one for positioning in front of each eye of the user, the embodiments herein illustrated present a goggle, goggles, and/or pair of goggles that have a single lens structure that extends between and in front of both eyes of the user.

As illustrated, the lens 10 is retained within the frame 124, the lens edge 16 configured to register in a groove 126 in the frame 124 to securely retain the lens 10 within the frame 124 in most situations other than when a user wishes to remove the lens 10, such as when the user wishes to replace the lens 10. As discussed previously, the lens edge 10 can include nose tabs 18 and forehead tabs 20 configured to register with reciprocal features in the groove 126 of the frame 124 to increase the ability of the frame 124 to secure the lens 10 from undesired removal.

The vents 22 allow venting air 50 to flow through porous foam 24 into the interior space 124 defined by the lens 10, the frame 124 and the user's face as discussed above.

The frame 124 includes securing means 110 for securing the lens 10 proximate the user's face and eyes and, more generally, about the user's head. The securing means 110 illustrated in FIGS. 8 through 11 is a woven, super Jacquard strap which stretches preferentially in one direction—in this instance along the long axis of the strap, i.e., horizontally, but exhibits little to no stretch in the vertical direction. For example, an exemplary embodiment of the super Jacquard weave strap is one that stretches from about 60% to 90% beyond its original length in the horizontal direction, but only stretches from about 10% to about 30% of its original height in the vertical direction, while returning approximately to its original length and width when the stretching force is removed. Of course, straps made of other materials, including strings, rubber, elastic, other weaves of material, and the like fall within the scope of the disclosure. Additionally, in other embodiments, such as safety or sunglasses, the securing means include arms (adjustable, flexible, and rigid), hinges (such as those that allow a lens to flip down from a safety helmet or other headwear), attachments for visors, such as in a military pilot's helmet, and other securing means known in the art. The securing means 110 in this instance have a clip 120 configured to register with a post 122 on the frame 124, but other means of attaching the securing means to the frame 124 exist, as discussed above. The clip 120-post 122 arrangement allows the securing means 110 in this embodiment to adjust to whether a user is wearing the goggle 100 with or without a helmet.

The securing means (strap) 110 illustrated includes a strap outer side 112 and a strap inner side 114 opposite the strap outer side 112. The strap inner side 114 optionally includes gripping material 116 made of rubber, elastomer, or other thermoplastic positioned on the strap inner side to provide increased friction with the strap inner side 114 against a helmet or a user's head and, thereby, reducing the likelihood of the securing means 110 from slipping or otherwise moving out of position. While the gripping material 116 is illustrated as three lines approximately equidistant apart across the height of the securing means 110, other configurations of gripping material, such as patterns of dots and other geometric patterns, fall within the scope of the disclosure.

Finally the securing means 110 optionally includes a means of adjusting the length of the securing means 110 to allow a user to individually adjust the securing means 110 to best fit around his or her head and/or helmet. While FIGS. 8 through 11 illustrate buckles 118 to adjust the length of the securing means 110, other means of adjusting the securing means 110 includes the use of elastic materials and weaves of fabrics, hook and loop fasteners, snaps, strings for tying, and other methods known in the art.

The upper frame vents 128 and upper frame vent foam 130 as discussed above are best illustrated in FIGS. 9 and 10. Similarly, lower frame vents 129 and lower frame vent foam 131, also previously discussed, are best illustrated in FIG. 11.

The porous upper frame vent foam 130 and lower frame vent foam 131 allow the venting air 50 to escape from the interior space 140 of the frame 124 while minimizing or preventing snow, particulate matter, and other environmental irritants from entering the interior space 140. The upper and lower frame vent foam 130, 131 can be bonded to the frame 124 with various bonding agents as known in the art and as discussed above.

The frame 100 optionally includes sealing foam 132 that helps create a seal between the frame 124 and a user's face. Sealing foam 132 provides a flexible and generally weather proof seal about the user's face and better adjusts, with a flexible frame 124 and lens 110, to the shape of different users' faces.

The sealing foam 132 optionally comprises a plurality of different foams and other materials instead of just a single foam. For example, an embodiment of the sealing 132 illustrated in FIGS. 8 through 11 includes an outer fleece layer 134, a middle foam layer 136, and an inner foam layer 138.

The outer fleece layer 134 provides warmth and comfort against a user's skin while wicking moisture away from the user's face.

The middle foam layer 136 is bonded to the outer fleece layer 134 with bonding agents, such as adhesives, glues, chemical fixants, and the like. The middle foam layer 136 is a relatively more porous layer than the outer fleece layer 134. The middle foam layer 136 helps to quickly wick and absorb moisture from the outer fleece layer 134 and more quickly dissipate the moisture to the ambient air than would the outer fleece layer 134. Removing the moisture from proximate the user's face improves the user's comfort.

The third frame, or inner, foam layer 138 is bonded to the middle foam layer 136 and the frame 124 with bonding agents as discussed above. The frame foam layer 138 is a denser, i.e., less porous, foam than the middle foam layer 136. The denser frame foam layer 138 provides increased stability and better maintains its shape, thereby improving its ability to adhere to the frame 124 as the frame 124 flexes.

While the embodiments illustrated in FIGS. 2 through 11 relate to a goggle particularly adapted for outdoor use such as in skiing and snowboarding, other embodiments include safety glasses and goggles, visors for helmets, and other similar uses fall within the scope of the disclosure.

Methods of manufacturing embodiments of the invention are also disclosed herein. The method includes providing a first layer and a second layer of flat, transparent thermoplastic, such as polycarbonate. A first, polarized film is provided also provided. A chemical fixant, such as a bonding agent described above, is applied to at least part of one of the first layer and the polarized film. The polarized film is applied to the first layer such that polarized film adheres to the first layer. Of course it will be understood that the polarized film can be adhered to the second layer alternatively. A photochromatic film is also provided. A bonding agent is applied to at least part of one of the polarized film and the photochromatic film. The photochromatic film then is adhered to the polarized film. Of course, it will be understood that the photochromatic film can be adhered to the second layer initially instead of the polarized film. A bonding agent is applied to at least of the part of the photochromatic film and the second layer, which are then adhered together to form the embodiment illustrated in FIG. 1 in cross-section. Other arrangements and orders of combining the first layer, the second layer, the polarized film and the photochromatic film fall within the scope of the disclosure to form the lens 10.

The initially flat lens 10 is then thermoformed in a mold of a selected shape under a selected temperature and pressure to provide a selected radius of curvature in at least one of the horizontal and the vertical axis as described above. The process of forming the radius of curvature from a flat lens 10 occurs without causing any wrinkling, crackling, lines, cracking, and other defects in the lens 10 and the polarized film 48 and the photochromatic film 46 within the tolerances of the manufacturing process.

A frame for securing and positioning the lens 10 proximate a user's eyes is also provided, the frame including securing means to hold the frame and lens in position about the user's head. The frame provided optionally includes a flexible thermoplastic, such as polyurethane, formed in a mold.

The one or more present inventions, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure.

The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A goggle for use in cold weather, said goggle comprising:
    a frame configured for holding and positioning a lens proximate an eye of a user;
    securing means associated with said frame for holding said frame proximate said eye of said user;
    said lens formed and sized to extend about said eye to cover said eye and an eye area, said lens being formed to have a generally arcuate shape with a major axis extending generally from one side to another side of said user's head in alignment with said user's eyes and with a minor axis extending from said user's forehead downward toward said user's cheeks, said lens including,
        a first layer made of a first transparent thermoplastic material;
        a second layer made of a second transparent thermoplastic material, said second layer and said first layer being laminated to each other;
        a polarized film that is translucent and configured to filter a preselected amount of light passing therethrough, said polarized film being laminated to one of said first layer and said second layer;
        a photochromatic film laminated to one of said first layer, said second layer and said polarized film; said photochromatic film being configured to vary an amount of light passing therethrough in response to ultraviolet radiation received by said photochromatic film;
        wherein at least one of said polarized film and said photochromatic film is substantially free of at least one of visible stretching, wrinkling, cracking, crackling, and lines.

2. The goggle of claim 1, wherein said polarized film and said photochromatic film are positioned adjacent each other between said first layer and said second layer.

3. The goggle of claim 1, wherein said first layer and said second layer comprise a flexible polycarbonate.

4. The goggle of claim 1, wherein said lens has a thickness from about 0.5 millimeters to about 2.0 millimeters.

5. The goggle of claim 1, further comprising an anti-fog lens spaced apart from said second layer to provide an air space therebetween.

6. The goggle of claim 5, wherein said anti-fog lens comprises a thermoplastic layer selected from one of an acetate, polycellulose acetate, cellulose acetate, cellulose acetobutyrate, and a cellulose acetopropionate.

7. The goggle of claim 1, wherein said lens has a width from about 180 millimeters to about 240 millimeters.

8. The goggle of claim 1, wherein said lens has a height from about 75 millimeters to about 135 millimeters.

9. The goggle of claim 1, wherein said arcuate shape includes a curvature from about 3 base curve number to about 9 base curve number in said major axis.

10. The goggle of claim 1, wherein said arcuate shape includes a curvature from about 1 base curve number to about 7 base curve number in said minor axis.

11. The goggle of claim 1, wherein said lens is thermoformed in a mold of a selected shape as a single piece.

12. The goggle claim 1, wherein said photochromatic film is provided with a tint of a selected color to enhance visual acuity and contrast of an object that a user views through said lens assembly.

13. The goggle of claim 12, wherein said tint is configured to vary said color in response to a received amount of ultraviolet radiation.

14. The goggle of claim 13, wherein said color varies from yellow-gray to one of rose-gray, rose-purple-gray, and purple-gray.

15. The goggle of claim 14, wherein said lens varies said amount of light passing therethrough from about 6 percent of available light to about 47 percent of available light in response to a received amount of ultraviolet radiation.

16. The goggle of claim 12, wherein said color is one of rose-gray, rose-purple-gray, and purple-gray.

17. The goggle of claim 16, wherein said lens varies said amount of light passing therethrough from about 6 percent of available light to about 40 percent of available light in response to a received amount of ultraviolet radiation.

18. The goggle of claim 1, wherein said lens is replaceable by said user.

19. A lens that varies an amount of light passing therethrough in response to ultraviolet radiation received by said lens, comprising:
   first layer made of a transparent thermoplastic and a second layer made of a transparent thermoplastic laminated thereto;
   a polarized film configured to filter light passing through said lens, said polarized film positioned between and laminated to at least one of said first layer and said second layer; and,
   a photochromatic film configured to vary an amount of light transmitted therethrough in response to a received amount of ultraviolet radiation, said photochromatic film positioned between and laminated to at least one of said first layer, said second layer, and said polarized film;
   said lens being formed to have a generally arcuate shape with a major axis extending generally along a horizontal axis and with a minor axis extending generally along a vertical axis;
   wherein at least one of said polarized film and said photochromatic film is substantially free of at least one of visible stretching, wrinkling, cracking, crackling, and lines.

20. The lens of claim 19, wherein said lens varies said amount of light passing therethrough from about 6 percent of available light to about 40 percent of available light in response to said received amount of ultraviolet radiation.

21. The lens of claim 19, wherein said lens varies said amount of light passing therethrough from about 6 percent of available light to about 47 percent of available light in response to said received amount of ultraviolet radiation.

22. A method of making a lens that varies the amount of light passing therethrough in response to ultraviolet radiation received by said lens, comprising:
   providing a first layer made of a transparent thermoplastic material;
   providing a second layer made of transparent thermoplastic material;
   positioning and laminating a polarized film configured to filter reflected light passing through said lens to at least one of said first layer and said second layer;
   positioning and laminating a photochromatic film configured to vary an amount of light transmitted therethrough in response to a received amount of ultraviolet radiation to one of said first layer, said second layer, and said polarized film;
   laminating said first layer and said second layer together such that said polarized film and said photochromatic film are positioned adjacent to each other and between said first layer and said second layer; and,
   thermoforming said lens in a mold of selected shape as a single piece to have a generally arcuate shape with a major axis extending generally along a horizontal axis and with a minor axis extending generally along a vertical axis, wherein at least one of said polarized film and said photochromatic film is substantially free of at least one of visible stretching, wrinkling, cracking, crackling, and lines.

23. A lens that varies the amount of light passing therethrough in response to ultraviolet radiation received by said lens, comprising:
   a first layer that is transparent and configured to vary an amount of light transmitted therethrough in response to a received amount of ultraviolet radiation;
   a second layer made of a transparent thermoplastic laminated to said first layer;
   a polarized film configured to filter light passing through said lens, said polarized film positioned between and laminated to at least one of said first layer and said second layer, said polarized film being substantially free of at least one of visible stretching, wrinkling, cracking, crackling, and lines; and,
   said lens being formed to have a generally arcuate shape with a major axis extending generally along a horizontal axis and with a minor axis extending generally along a vertical axis.

24. The lens of claim 23, wherein said first layer further comprises a photochromatic film positioned between and laminated to at least one of said first layer and said polarized film, said photochromatic film being substantially free of at least one of visible stretching, wrinkling, cracking, crackling, and lines.

25. The lens of claim 24, wherein said first layer further comprises a thermoplastic.

* * * * *

UNITED STATES PATENT AND TRADEMARK OFFICE
CERTIFICATE OF CORRECTION

PATENT NO. : 8,356,895 B2  
APPLICATION NO. : 12/812457  
DATED : January 22, 2013  
INVENTOR(S) : Eleanor Wink Jackson et al.

Page 1 of 1

It is certified that error appears in the above-identified patent and that said Letters Patent is hereby corrected as shown below:

In the Claims

In column 14, claim 12, line 48, after "The goggle" insert --of--.

Signed and Sealed this
Twelfth Day of May, 2015

Michelle K. Lee
*Director of the United States Patent and Trademark Office*